United States Patent
Huang et al.

(10) Patent No.: US 11,365,248 B2
(45) Date of Patent: Jun. 21, 2022

(54) FORMULATION OF TOCILIZUMAB AND METHOD FOR TREATING COVID-19 BY INHALATION

(71) Applicant: ANOVENT PHARMACEUTICAL (U.S.), LLC, Newark, NJ (US)

(72) Inventors: Cai Gu Huang, Shrewsbury, MA (US); Hitesh Bhagavanbhai Mangukiya, Shanghai (CN)

(73) Assignee: ANOVENT PHARMACEUTICAL (U.S.), LLC, Newark, NJ (US)

( * ) Notice: Subject to any disclaimer, the term of this patent is extended or adjusted under 35 U.S.C. 154(b) by 0 days.

(21) Appl. No.: 17/361,651

(22) Filed: Jun. 29, 2021

(65) Prior Publication Data

US 2021/0403550 A1 Dec. 30, 2021

Related U.S. Application Data

(60) Provisional application No. 63/045,225, filed on Jun. 29, 2020.

(51) Int. Cl.
| | | |
|---|---|---|
| C07K 16/24 | (2006.01) | |
| A61K 47/18 | (2017.01) | |
| A61K 47/26 | (2006.01) | |
| A61K 9/00 | (2006.01) | |
| A61K 39/00 | (2006.01) | |

(52) U.S. Cl.
CPC .......... *C07K 16/248* (2013.01); *A61K 9/0078* (2013.01); *A61K 47/183* (2013.01); *A61K 47/26* (2013.01); *A61K 2039/505* (2013.01); *A61K 2039/545* (2013.01); *C07K 2317/94* (2013.01)

(58) Field of Classification Search
CPC .............. C07K 16/248; C07K 2317/94; A61K 9/0078; A61K 47/183; A61K 47/26; A61K 2039/505; A61K 2039/545
See application file for complete search history.

(56) References Cited

U.S. PATENT DOCUMENTS

| | | | |
|---|---|---|---|
| 5,230,884 A | 7/1993 | Evans et al. | |
| 5,654,007 A | 8/1997 | Johnson et al. | |
| 2012/0301460 A1 | 11/2012 | Bao et al. | |
| 2018/0133375 A1* | 5/2018 | Shiozaki | A61L 31/048 |
| 2019/0030268 A1 | 1/2019 | Huang | |
| 2019/0218300 A1* | 7/2019 | Del Rio | A61K 47/26 |
| 2019/0262450 A1* | 8/2019 | Jezek | A61P 37/00 |
| 2021/0101987 A1* | 4/2021 | Jayaraman | C07K 16/2866 |
| 2021/0284743 A1* | 9/2021 | Shailubhai | A61K 47/26 |

FOREIGN PATENT DOCUMENTS

| | | |
|---|---|---|
| WO | 2012050945 A1 | 4/2012 |
| WO | 2017035415 A1 | 3/2017 |
| WO | 2018071655 A1 | 4/2018 |
| WO | 2018078162 A1 | 5/2018 |
| WO | 2020041301 A1 | 2/2020 |

OTHER PUBLICATIONS

Respaud R, et al. (Jun. 2015) Expert Opin Drug Deliv. 12(6):1027-39. (doi: 10.1517/17425247.2015.999039).*
Reespaud R, et al. (2014) mAbs. 6(5):1347-1355. (doi: 10.4161/mabs.29938).*
International Search Report and Written Opinion issued in International Application No. PCT/US21/39520 with an international filing date of Jun. 29, 2021, and dated Oct. 12, 2021.

* cited by examiner

*Primary Examiner* — Robert S Landsman
(74) *Attorney, Agent, or Firm* — Parker Poe Adams & Bernstein LLC (57) ABSTRACT

The present invention is directed to formulations containing the anti-IL-6 therapeutic monoclonal antibody tocilizumab and pharmaceutically acceptable excipients that can be administered using a soft mist inhaler or a nebulizer.

5 Claims, 2 Drawing Sheets

FORMULATION OF TOCILIZUMAB AND METHOD FOR TREATING COVID-19 BY INHALATION

PRIORITY STATEMENT

This application claims the benefit of the filing date of U.S. Provisional Patent Application No. 63/045,225, filed on Jun. 29, 2020, which is incorporated herein by reference in its entirety.

BACKGROUND OF THE INVENTION

A novel coronavirus, referred to as Severe Acute Respiratory Syndrome Coronavirus 2 (SARS-Cov-2), was first reported in China as the cause of COVID-19, exhibits a spectrum of symptoms that can vary from mild to critical. Pneumonia appears to be the most frequent serious manifestation of infection and approximately 6-10% of patients develop Acute Respiratory Distress Syndrome (ARDS), requiring continuous positive airway pressure therapy or mechanical ventilation.

No specific therapeutic treatment has proved successful, other than supportive care. The actual "standard of care" (SOC) includes off-label and compassionate use therapies, such as hydroxychloroquine, while steroid administration remains controversial. Monoclonal antibodies, convalescent plasma and novel antiviral drugs such as remdesivir are used in selected patients. However, several drugs that have been highly promising in vitro have failed in clinical trials. There is a need in the art to develop a formulation and an effective method for treating COVID-19 by inhalation.

Although COVID-19 pathogenesis is still unclear, some patients with a severe disease exhibit laboratory evidence of a systemic inflammation similar to cytokine release syndrome (CRS). CRS is characterized by a sharp increase in the number of proinflammatory cytokines, among which IL-6 plays a pivotal role. Therefore, blocking the IL-6 pathway might reduce the vigorous inflammatory response in COVID-19.

Xiaoling Xu et. al. analyzed the immune characteristics of patients with severe coronavirus disease 2019 (COVID-19), they have identified pathogenic T cells and inflammatory monocytes with large amounts of interleukin 6 secretion as possibly inciting the inflammatory storm, which may potentially be curbed by monoclonal antibodies that target the IL-6 pathways.

ACTEMRA® (tocilizumab) is a recombinant humanized monoclonal antibody of the immunoglobulin IgG1 subclass that targets both forms of the IL-6 receptor (membrane-bound and soluble) (US20120301460A1). It has been used in adults and children to treat rheumatological conditions such as rheumatoid arthritis and other autoinflammatory conditions, or in patients with CRS induced by chimeric antigen receptor T-cell therapy. Tocilizumab 8 mg/kg IV has been approved for use in rheumatoid arthritis, including in Japan and Europe. Currently, tocilizumab has been approved by the USFDA in a strength of 20 mg per mL for IV administration (80 mg per 4 mL, 200 mg per 10 mL, and 400 mg per 20 mL). Tocilizumab is indicated for the treatment of adult patients with moderate to severe active rheumatoid arthritis who have had an inadequate response to one or more Disease-Modifying Anti-Rheumatic Drugs (DMARDs). Tocilizumab is also indicated for the treatment of active polyarticular juvenile idiopathic arthritis as well as active systemic juvenile idiopathic arthritis in patients 2 years of age and older.

The efficacy of tocilizumab has been assessed in severe patients with COVID-19 as a therapeutic strategy. Patients diagnosed as having severe or critical COVID-19 in The First Affiliated Hospital of University of Science and Technology of China (Anhui Provincial Hospital) and in Anhui Fuyang Second People's Hospital were given tocilizumab in addition to routine therapy between 5 and 14 Feb. 2020. In patients with coronavirus disease 2019, a large number of T lymphocytes and mononuclear macrophages were activated, producing cytokines such as interleukin-6 (IL-6), which bind to the IL-6 receptor on the target cells, causing the cytokine storm and severe inflammatory responses in the lungs and other tissues and organs. Tocilizumab, as a recombinant humanized antihuman IL-6 receptor monoclonal antibody, can bind to the IL-6 receptor with high affinity, thus preventing IL-6 itself from binding to its receptor, rendering it incapable of immune damage to target cells, and alleviating the inflammatory responses.

COVID-19 is a newly occurring infectious respiratory disease with mild symptoms in the early stages of infection. However, in a considerable number of patients, the symptoms deteriorate rapidly and are manifested as chest tightness, shortness of breath, and even respiratory failure. CT scans often show rapid enlarged opacities. These patients usually need oxygen therapy and even assisted ventilation in the ICU. Unfortunately, 4.3 to 11% of them die even after recommended standard treatment, as no effective therapy was available. After treatment with tocilizumab, in addition to improvement of body temperature, the respiratory function was improved to some degree in most of the patients. Chest tightness was relieved. Most patients lowered their oxygen intake flow, and their oxygen saturation remained stable. The systemic administration showed significant efficacy, so it is recommended to start tocilizumab treatment as soon as possible when the following conditions occur: persistent fever, condition changes from mild to severe (including high-risk factor for severe cases), diffuse lung opacities on CT scans, and elevated levels of IL-6. Early treatment can effectively control the deterioration of symptoms.

The decrease in the percentage of lymphocytes has been considered an important diagnostic indicator for reduced severity in COVID-19 patients. In our study, a lower percentage of lymphocytes was found in 85.0% of patients (17/20) and returned to normal in 52.6% of patients (10/19) within 5 days when tocilizumab was given. At the same time, elevated CRP also returned to normal. The level of IL-6 increased in all patients before treatment. After treatment, IL-6 levels temporarily increase in serum over the next few days, because its receptors have been blocked by tocilizumab. Similar conditions can be observed in chimeric antigen receptor T cell treatment. The lung opacities on CT scans were absorbed in 19 (90.5%) patients. Considering that damaged lung tissue needs sufficient time to repair, remission delay in CT scan can be anticipated. During the treatment, no adverse drug reactions or subsequent pulmonary infections were reported. Clinical symptoms of all patients improved remarkably with good prognosis after treatment. All patients have been discharged, with most of them being discharged within 2 week after tocilizumab treatment. Therefore, tocilizumab can effectively treat patients afflicted with severe COVID-19, which might be explained by the blocking of IL-6-associated febrile and inflammatory storm response.

The systemic intravenous administration of tocilizumab exposes the entire body to the drug and, as a result, the patient usually experiences severe toxic side effects. The adverse reactions to tocilizumab includes serious infections, gastrointestinal perforations, infusion reactions (injection site infections), anaphylaxis, neutropenia, thrombocytopenia, elevated liver enzymes, immunogenicity, and sometimes malignancies.

As part of the Biologics Price Competition and Innovation Act (BPCIA), a biological drug product (produced in or derived from living organisms) may be demonstrated to be "biosimilar" if data show that, among other things, the product is "highly similar" to an already-approved biological product. The biosimilar product should retain at least the biologic function and treatment efficacy of the U.S. Food and Drug Agency-approved biological product. The biological product can be formulated differently, however, from the approved biological product. The formulation can improve stability and shelf storage of the biologic drug product, and can also improve efficacy in treating a particular disease or condition. The formulation can also improve other aspects of administration, including a reduction in patient discomfort or other unwanted effects that a patient may experience upon administration of the approved biological product. Antibody molecules can be produced as a biosimilar, and reformulated accordingly. There remains a need in the art for a high quality antibody formulation, method of administration, and use thereof.

The major route of entry of COVID-19 infection is through nasopharynx/oropharynx. Waradon Sungnak et. al. discovered that mucus-producing goblet cells and ciliated cells in the nose had the highest levels of COVID-19 virus proteins, of all cells in airways, which makes these cells the most likely infection route for the virus. The concept of local drug delivery through inhalation is proposed as a method for delivering high drug concentrations to the primary infection site as early as possible while preventing exposure of vital organs to toxic drug concentrations in the systemic circulation. In this way, systemic side effects are minimized. The respiratory system has a large surface area, thin alveolar epithelium, rapid absorption, lack of first-pass metabolism, high bioavailability, and the capacity to absorb large quantities of drug, making it an optimal route for drug administration (Labiris and Dolovich 2003).

It is clinically advantageous to use a liquid formulation of tocilizumab administered using suitable inhalers, including soft mist inhalers and nebulizers, in order to achieve localized delivery of the active substance to the lungs. Moreover, it is important to increase the lung deposition of a drug delivered by inhalation using soft mist inhalation or nebulization. Therefore, it is essential when administering an effective COVID-19 drug by inhalation to maximize lung deposition of the drug. Soft mist inhalation devices or other nebulization devices can significantly increase the lung deposition of liquid tocilizumab formulations thereby increasing the efficacy of the drug against COVID-19 primary infection.

The main objective when formulating a therapeutic monoclonal antibody tocilizumab solution for administration using an inhaler is to increase the efficacy of the tocilizumab, thereby increasing effectiveness while reducing side effects associated with intravenous infusion treatment in COVID-19 patients. The general disadvantage of therapeutic monoclonal antibody intravenous infusion is its route of administration, high dose and stability; as once the infusion is prepared it has to be administered through an intravenous line as soon as possible because it can be stored for only 24 hours in a refrigerator at 2° C. to 8° C. (36° F. to 46° F.) or 8 hours at room temperature.

SUMMARY OF THE INVENTION

The present invention is directed to formulations of the anti-IL-6 therapeutic monoclonal antibody tocilizumab and pharmaceutically acceptable excipients, such as, but not limited to, disodium phosphate dodecahydrate, sodium dihydrogen phosphate dehydrate, polysorbate 80, and sucrose and to a novel therapeutic strategy for the treatment of COVID-19 by administering the formulations as a soft mist inhaler solution and/or nebulizer solution. The biopharmaceutical formulations according to the invention have to meet high quality standards.

One aspect of the present invention is to provide a biopharmaceutical formulation containing the therapeutic monoclonal antibody tocilizumab and pharmaceutically acceptable excipients, which can be administered as an aerosol by optimal nebulization of a solution using a soft mist inhaler. The stability of the formulated solution is a storage time of few years, preferably one year, more preferably two years. In one embodiment, the formulation has a storage time of at least about 6 months at a temperature from ranging from about 2° C. to about 8° C. ° C. In one embodiment, the formulation has a storage time of at least about 1 year at a temperature ranging from about 2° C. to about 8° C. ° C. In one embodiment, the formulation has a storage time of at least about 2 years at a temperature ranging from about 2° C. to about 8° C.

Another aspect of the invention is to provide a biopharmaceutical formulation that is a solution comprising tocilizumab and excipients that can be nebulized by an inhaler device, such as a pressurized metered dose inhaler, digital metered dose inhaler, or nebulizer, wherein the aerosol produced by the device falls reproducibly within a specified range of particle size.

Another aspect of the present invention is to provide biopharmaceutical formulations that are solutions comprising tocilizumab and excipients that can be administered by nebulization using an ultra-sonic based or air pressure based nebulizer/inhaler. The stability of the formulation should be a storage time of few years, preferably one year, more preferably two years. ° C. In one embodiment, the formulation has a storage time of at least about 6 months at a temperature ranging from about 2° C. to about 8° C. ° C. In one embodiment, the formulation has a storage time of at least about 1 year at a temperature ranging from about 2° C. to about 8° C. ° C. In one embodiment, the formulation has a storage time of at least about 2 years at a temperature ranging from about 2° C. to about 8° C.

Another aspect of the present invention is to provide biopharmaceutical formulations that are solutions comprising tocilizumab and excipients that can be administered by inhalation. In one embodiment, the solution is administered as aerosolized particles that have a mass median diameter of less than about 5 microns. This size of aerosolized particle is able to penetrate the lungs when administered by inhalation.

An important aspect of the current invention is to provide dosage forms containing an anti-inflammatory therapeutic monoclonal antibody, such as tocilizumab, and pharmaceutically acceptable excipients that can be administered as an aerosol and is effective at treating respiratory infections caused by SARS-CoV.

Another aspect of the current invention is to provide stable biopharmaceutical formulations containing tocilizumab and other excipients that can be delivered in the form of an aerosol by soft mist inhalation using an atomizer inhaler or nebulizer, which has substantially long term stability. In one embodiment, the formulation has a storage time of at least about 6 months at a temperature ranging from about 2° C. to about 8° C. In one embodiment, the formulation has a storage time of at least about 1 year at a temperature ranging from about 2° C. to about 8° C. In one embodiment, the formulation has a storage time of at least about 2 years at a temperature ranging from about 2° C. to about 8° C.

A further aspect of the current invention is to provide a method or process to prepare the above mentioned formulations of tocilizumab and excipients.

DETAILED DESCRIPTION OF THE INVENTION

It is necessary to use an inhalation formulation, in order to achieve better and significant delivery of a therapeutic monoclonal antibody to the lung. Furthermore, it is important to increase the lung deposition of a drug delivered by an inhalation method.

There is a need in the art to improve the drug delivery through inhalation by significantly increasing lung deposition. The soft mist or nebulization inhalation device disclosed in US20190030268 can significantly increase the lung deposition of inhalable drugs. This inhaler can nebulize a small amount of a liquid formulation into an aerosol that is suitable for therapeutic inhalation within a few seconds. These inhalers are particularly suitable for this liquid formulation.

In one embodiment, the soft mist devices useful for administering the biopharmaceutical formulation of the present invention are those in which an amount of less than about 70 microliters of formulation can be nebulized in one puff so that the inhalable part of aerosol corresponds to the therapeutically effective quantity of the drug. In one embodiment, the soft mist devices useful for administering the biopharmaceutical formulation of the present invention are those in which an amount of less than about 30 microliters of formulation can be nebulized in one puff so that the inhalable part of aerosol corresponds to the therapeutically effective quantity of the drug. In one embodiment, the soft mist devices useful for administering the biopharmaceutical formulation of the present invention are those in which an amount of less than about 15 microliters of formulation can be nebulized in one puff so that the inhalable part of aerosol corresponds to the therapeutically effective quantity of the drug. In one embodiment, the average particle size of the aerosol formed from one puff is less than about 15 microns. In one embodiment, the average particle size of the aerosol formed from one puff is less than about 10 microns. In one embodiment, average particle size of the aerosol formed from one puff ranges from about 5 microns to about 10 microns. In one embodiment, the average particle size of the aerosol formed from one puff is about 5 microns.

In one embodiment, the nebulization devices useful for administering the biopharmaceutical formulation of the present invention are those in which an amount of less than about 8 milliliters of biopharmaceutical solution can be nebulized in one puff so that the inhalable part of aerosol corresponds to the therapeutically effective quantity. In one embodiment, the nebulization devices useful for administering the biopharmaceutical formulation of the present invention are those in which an amount of less than about 2 milliliters of biopharmaceutical solution can be nebulized in one puff so that the inhalable part of aerosol corresponds to the therapeutically effective quantity. In one embodiment, the nebulization devices useful for administering the biopharmaceutical formulation of the present invention are those in which an amount of less than about 1 milliliters of biopharmaceutical solution can be nebulized in one puff so that the inhalable part of aerosol corresponds to the therapeutically effective quantity. In one embodiment, the average particle size of the aerosol formed from one puff is less than about 15 microns. In one embodiment, the average particle size of the aerosol formed from one puff is less than about 10 microns. In one embodiment, average particle size of the aerosol formed from one puff ranges from about 5 microns to about 10 microns. In one embodiment, the average particle size of the aerosol formed from one puff is about 5 microns.

A device of this kind for the propellant-free administration of a metered amount of a liquid pharmaceutical composition for inhalation is described in detail in, for example, US20190030268, entitled "inhalation atomizer comprising a blocking function and a counter".

The pharmaceutical formulation in the nebulizer is converted into an aerosol destined for the lungs. The nebulizer uses high pressure to spray the pharmaceutical formulation.

The pharmaceutical formulation, which can be a solution, is stored in a reservoir in this kind of inhaler. The formulations must not contain any ingredients which might interact with the inhaler to affect the quality of the pharmaceutical formulation or of the aerosol produced. In addition, active substances in the pharmaceutical formulations are very stable when stored and can be administered directly.

One aspect of the present invention is to provide a biopharmaceutical formulation containing the therapeutic monoclonal antibody tocilizumab and other excipients, which meets the high standards needed in order to achieve optimal nebulization of the formulation using a soft mist inhaler or nebulizer. The formulations have a storage time of few years, preferably at least one year, more preferably at least two years.

In one embodiment, the present invention is directed to a biopharmaceutical formulation comprising the therapeutic monoclonal antibody tocilizumab as an active substance in combination with other excipients, which can be a solution, which can be administered by soft mist inhalation and/or nebulization.

In one embodiment, the invention provides a method for treating a SARS-CoV infections including, but not limited to the COVID-19 virus infection, in humans by administering the formulation to a patient by inhalation. In one embodiment, the current invention provides a stable biopharmaceutical formulation containing a therapeutic monoclonal antibody, such as tocilizumab, in functional form with inactive ingredients, which meets the requirements needed to achieve optimal nebulization of the formulation using a soft mist inhaler and/or a nebulizer. It is important to provide the most stable formulation so as to keep the therapeutic monoclonal antibody functional for the labeled dosage. Another aspect is to provide a propellant-free suspension containing the therapeutic monoclonal antibody tocilizumab and other excipients, which can be nebulized under pressure using a soft mist or nebulization inhaler device. The aerosol produced by the device falls reproducibly within a specified range for particle size.

In another aspect, the invention provides a method for treating a condition in a subject comprising administering to a subject in need thereof an effective amount of the biopharmaceutical formulation described herein. In one embodiment, the condition is a COVID-19 infection. In one embodiment, the condition is a SARS-CoV infection.

In another aspect, the invention relates to a method of inhibiting COVID-19 infection or progression in a subject who has a mild or severe SARS-CoV-2 infection comprising administering to the subject an effective amount of the biopharmaceutical formulation with a soft mist inhaler or nebulizer as described herein.

In another aspect, the invention relates to a method of providing a tocilizumab-containing aerosol that can deliver tocilizumab to a user/patient at an inhalation or air flow rate that is effective at treating COVID-19 and other viral infections that target the respiratory system and hence causes damage to respiratory organs.

In another aspect, the present disclosure provides a method for enhancing the immunogenicity or therapeutic effect of a drug typically administered by vaccine by delivering the drug by soft mist inhalation or nebulization for the treatment of a COVID-19 infection in a patient. In one embodiment, the patient is a human. The method comprises administering an effective amount of antibodies as provided in the present disclosure.

Preferably, the antibody is a full-length tocilizumab antibody, comprising both variable and constant regions, although in some aspects, the antibody may comprise a derivative, fragment, or portion of a full-length antibody that retains the antigen-binding specificity. In one embodiment, the derivative, fragment, or portion retains most or all of the affinity of the full length antibody molecule. In one embodiment, the antibody comprises post-translational modifications (PTMs) or moieties, which may impact antibody activity or stability. In one embodiment, the antibody is methylated, acetylated, glycosylated, sulfated, phosphorylated, carboxylated, and/or amidated, or may comprise other moieties that are well known in the art. In one embodiment, the formulation comprises a therapeutically effective amount of the antibody.

In any type of pathogenic infection, lung mucociliary clearance is the primary mechanism by which the airways are kept clean from particles present in the liquid film that coats them. The conducting airways are lined with ciliated epithelium that beat to drive a layer of mucus towards the larynx, clearing the airways from the lowest ciliated region in about 24 hours. The fluid coating consists of water, sugars, proteins, glycoproteins, and lipids. The fluid is generated in the airway epithelium and the sub-mucosal glands, and the thickness of the layer ranges from several microns in the trachea to approximately 1 micron in the distal airways in humans, rats, and guinea pigs.

A second important mechanism for keeping the lungs clean is via momentum transfer from air flowing through the lungs to the mucus coating. Coughing increases this momentum transfer and is used by the body to aid in removal of excess mucus. It becomes important when mucus cannot be adequately removed by ciliary beating alone, as occurs in mucus hyper-secretion associated with many disease states. Air speed as high as 200 m/s can be generated during a forceful cough. For such high air speeds the onset of unstable sinusoidal disturbances at the mucus layer have been observed. This disturbance results in enhanced momentum transfer from the air to the mucus and consequently accelerates the rate of mucus clearance from the lungs.

Formulations have been developed to limit infections of the respiratory system, especially viral infections in the lung. In one embodiment, the formulations are an aqueous solution for enhanced delivery to the lung, which forms liquid aerosol particles of less than about 7 μm in diameter loaded with a high concentration of a therapeutic monoclonal antibody, such as tocilizumab, which reduces viral shedding.

Drug delivery by inhalation represents a mode of administration of low molecular weight pharmaceutical formulations for treating various lung diseases, with a generally noninvasive systemic delivery of drugs. Recently several biopharmaceutical companies have been developing methods for pulmonary delivery of peptides, proteins, and therapeutic monoclonal antibodies with one such product already in clinical use (the enzyme DNAse produced by Genentech for the treatment of symptoms of cystic fibrosis in children). There is no evidence that inhaling autologous proteins presents significant immune issues. Konstantinos Sapalidis et. al. recently studied the three immunotherapeutic drugs nivolumab, ipilimumab and pembrolizumab that can be produced as an aerosol generated from the formulation, which uses water as the drug solvent, using a jet-nebulizer and residual cup (Sapalidis, Zarogoulidis et al. 2018). However, there is a continuing need in the art to obtain safer and more effective treatments for virus infections in the respiratory system.

A number of pharmaceutical preparations for pulmonary delivery of drugs have been developed. For example, U.S. Pat. No. 5,230,884 to Evans et. al., discloses the use of reverse micelles for pulmonary delivery of proteins and peptides. Reverse micelles are formed by adding a small amount of water to a nonpolar solvent (e.g. hexane) to form micro-droplets. In this medium, a surfactant (detergent) will orient itself with its polar heads inward, so that they are in contact with the water and the hydrophobic tails outward. The tiny droplets of water are surrounded by surfactant, and the protein to be delivered is dissolved in the aqueous phase. U.S. Pat. No. 5,654,007 to Johnson et. al., discloses methods for making an agglomerate composition containing a medicament powder (e.g. proteins, nucleic acids, peptides, etc.) wherein a non-aqueous solvent binding liquid (a fluorocarbon) is used to bind the fine particles into aggregated units. The agglomerate composition has a mean size ranging from 50 to 600 microns and is allegedly useful in pulmonary drug delivery by inhalation.

A therapeutically effective amount of the antibody may vary, depending on the disease or condition being treated, and/or depending on the characteristics of the subject to which the antibody is administered, such as age, gender, height, weight, state of advancement or stage of the disease or condition, the number and efficacy of previous administrations, other therapeutic agents administered to the subject, and other characteristics that are known to the practitioner or that would otherwise be taken into account in determining appropriate dosing. In one embodiment, a therapeutically effective amount is an amount that is effective to treat COVID-19. The effective dose of the active pharmaceutical ingredient against COVID-19 depends on its bioavailability and clinical efficacy. For systemic administration, the effective dose of the tocilizumab against COVID-19 ranges from about 1 μg to about 800 mg per dose. In one embodiment, the effective dose of the tocilizumab against COVID-19 ranges from about 10 mg to about 500 mg per dose. In one embodiment, the effective dose of the tocilizumab against COVID-19 ranges from about 300 mg to about 500 mg per dose. In one embodiment, the effective dose of the tocilizumab against COVID-19 ranges from about 10 μg to about 600 µg per dose. In one embodiment, the effective dose of the tocilizumab against COVID-19 ranges from about 300 µg to about 500 µg per dose. In one embodiment, the effective dose of the tocilizumab against COVID-19 ranges from about 10 µg to about 100 µg per dose. In one embodiment, the effective dose of the tocilizumab against COVID-19 ranges from about 20 µg to about 50 µg per dose.

The term "medicament," as used herein, means an active drug for treating a respiratory viral infection, a SARS-CoV infection, a COVID-19 infection, or symptoms of these infections.

The term "pharmaceutical formulation," as used herein, means a preparation that is in such a form as to permit the biological activity of the active ingredient or ingredients to be effective, and which contain no additional components which are unacceptably toxic to a subject to which the formulation would be administered. In one embodiment, such formulations are sterile.

The phrase "sterile formulation," as used herein, means a formulation that is aseptic or free from all living microorganisms and their spores.

The phrase "stable formulation," as used herein, means a formulation in which all the protein therein essentially retains physical stability and/or chemical stability and/or biological activity upon storage at the intended storage temperature. In one embodiment the storage temperature ranges from about 2 to about 8° C. In one embodiment, the formulation essentially retains its physical and chemical stability, as well as its biological activity upon storage. In one embodiment, the formulation is stable following freezing (e.g., to −20° C.) and thawing of the formulation, for example following 1 or more cycles of freezing and thawing. Various analytical techniques for measuring protein stability are available in the art and are reviewed in, for example, Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography or capillary zone electrophoresis; SDS-PAGE analysis to compare reduced and intact antibody; evaluating biological activity or antigen binding function of the antibody; etc.

The term "stabilizer," as used herein, means an excipient, or mixture of two or more excipients, which stabilizes a pharmaceutical formulation. For example, the stabilizer can prevent instability due to freezing-thawing or other thermal-induced destabilization of the formulation. Exemplary stabilizers include, but are not limited to, amino acids, such as arginine or methionine (including derivatives thereof).

The term "surfactant," as used herein, means a pharmaceutically acceptable surface-active agent. In the formulation of the invention, the amount of surfactant is expressed as weight/volume. The most commonly used weight/volume is mg/mL. Suitable examples of pharmaceutically acceptable surfactants include, but are not limited to, polyoxyethylen-sorbitan fatty acid esters, polyethylene-polypropylene glycols, polyoxyethylene-stearates, polyoxyethylene alkyl ethers, e.g. polyoxyethylene monolauryl ether, alkylphenylpolyoxy-ethylene ethers (Triton-X), polyoxyethylene polyoxypropylene copolymer (Poloxamer, Pluronic), and sodium dodecyl sulfate (SDS). Examples of suitable polyoxyethylene sorbitan-fatty acid esters are polysorbate 20 (sold under the trademark TWEEN 20®) and polysorbate 80 (sold under the trademark TWEEN 80®). Examples of suitable polyethylene polypropylene copolymers are those sold under the names PLURONIC® F68 or POLOXAMER 1880®. Examples of suitable polyoxyethylene-stearates are those sold under the trademark MYRJ™. Examples of suitable polyoxy-ethylene alkyl ethers are those sold under the trademark BRIJ™. Examples of suitable alkylphenol-poly-oxyethylene ethers are those sold under the trade name TRITON-X®.

The term "buffer," as used herein, means a pharmaceutically acceptable compound that resists changes in pH by the action of its acid/base conjugate components. In one embodiment, the pH of the formulation ranges from about 5 to about 7. In one embodiment, the pH of the formulation ranges from about 5.5 to about 6.5. In one embodiment, the pH of the formulation is about pH 6. Selecting a suitable buffer achieves the desired pH of the formulation. Suitable pharmaceutically acceptable buffers include, but are not limited to, histidine-buffers, citrate-buffers, gluconate-buffers, succinate-buffers, acetate buffers, glycylglycine, and other organic acid buffers, and phosphate-buffers. In one embodiment, the buffer comprises L-histidine or mixtures of L-histidine with L-histidine hydrochloride. In one embodiment, the formulations include an isotonicity agent so that the formulation is isotonic. In one embodiment, the buffer is histidine (e.g. L-histidine).

The term "isotonic formulation," as used herein, means a formulation that has essentially the same osmotic pressure as human blood. Isotonic formulations will generally have an osmotic pressure ranging from about 250 mOsm to about 350 mOsm. Isotonicity can be measured, for example, using a vapor pressure or ice-freezing type osmometer.

The phrases "liquid formulation," as used herein, mean a formulation for inhalation according to the invention that is a liquid (solution for inhalation) at a temperature of at least about 2 to about 8° C. The phrases aqueous formulation," as used herein, mean a formulation for inhalation according to the invention that contains water.

The phrase "inhalation device," as used herein, means a device, such as soft mist inhaler, pressurized metered dose inhaler, nebulizer, digital metered dose inhaler, or other type of devise which is adapted or designed to administer a drug or pharmaceutical formulation by the inhalation route. In one embodiment, the inhalation device administers about 20 µL to about 4 mL of the pharmaceutical formulation. In one embodiment, the inhalation device administers about 25 µL to about 4 mL of the pharmaceutical formulation. In one embodiment, the inhalation device administers about 30 µL to about 4 mL of the pharmaceutical formulation. In one embodiment, the inhalation device administers about 50 µL to about 4 mL of the pharmaceutical formulation.

Therapeutic formulations of the antibodies for use in accordance with the present invention are prepared for storage for soft mist inhalation or nebulization by mixing an antibody having the desired degree of purity with optional pharmaceutically acceptable carriers, excipients or stabilizers (Remington's Pharmaceutical Sciences 16th edition, Osol, A. Ed. (1980)), in the form of a lyophilized formulation or an aqueous solution. Acceptable carriers, excipients, or stabilizers are nontoxic to recipients at the dosage and concentrations employed, and include, but are not limited to, buffers such as phosphate, citrate, and other organic acid; antioxidants including, but not limited to, ascorbic acid and methionine; preservatives (such as octadecyldimethylbenzyl ammonium chloride; hexamethonium chloride; benzalkonium chloride, benzethonium chloride; phenol; butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers, such as polyvinylpyrrolidone; amino acids, such as glycine, glutamine, asparagine, histidine, arginine, or lysine; monosaccharides; disaccharides; and other carbohydrates including, but not limited to, glucose, mannose, or dextrins; chelating agents, such as EDTA; sugars such as sucrose, mannitol, trehalose, and sorbitol; salt-forming counter-ions such as sodium; metal complexes (e.g. Zn-protein complexes); and/or non-ionic surfactants such as TWEENT™, PLURONICS™, and polyethylene glycol (PEG).

In one embodiment, the formulations contain more than one active compound. In one embodiment, the more than one active compounds are those with complementary activities that do not adversely affect each other. The type and effective amounts of such active compound depends, for example, on the amount of antibody present in the formulation, and the clinical parameters of the subject being treated.

In one embodiment, the formulations are used for in vivo administration through inhalation and are sterile. Sterility is readily accomplished by filtering the formulation through a sterile filtration membrane.

In one embodiment, the anti-IL-6R antibody-containing liquid formulation according to the present invention contains a high concentration of the anti-IL-6R antibody. In one embodiment, the formulation for inhalation, which can be a solution, comprises from about 1 mg/ml to about 300 mg/ml of the antibody. In one embodiment, the formulation for inhalation, which can be a solution, comprises from about 1 mg/ml to about 50 mg/ml of the antibody. In one embodiment, the formulation for inhalation, which can be a solution, comprises from about 50 mg/ml to about 100 mg/ml of the antibody. In one embodiment, the formulation for inhalation, which can be a solution, comprises from about 50 mg/ml to about 200 mg/ml of the antibody. In one embodiment, the formulation for inhalation, which can be a solution, comprises from about 150 mg/ml to about 3000 mg/ml of the antibody. In one embodiment, the formulation for inhalation, which can be a solution, comprises from about 4 mg/ml to about 12 mg/ml of the antibody. In one embodiment, the formulation for inhalation, which can be a solution, comprises from about 10 mg/ml to about 55 mg/ml of the antibody. In one embodiment, the formulation for inhalation, which can be a solution, comprises from about 5 mg/ml to about 30 mg/ml of the antibody. In one embodiment, the formulation for inhalation, which can be a solution, comprises from about 2 mg/ml to about 8 mg/ml of the antibody. In one embodiment, the formulation for inhalation, which can be a solution, comprises from about 55 mg/ml to about 65 mg/ml of the antibody. In one embodiment, the formulation for inhalation, which can be a solution, comprises from about 15 mg/ml to about 25 mg/ml of the antibody. In one embodiment, the formulation for inhalation, which can be a solution, comprises from about 5 mg/ml to about 15 mg/ml of the antibody. In one embodiment, the formulation for inhalation, which can be a solution, comprises from about 10 mg/ml to about 20 mg/ml of the antibody In one embodiment, the formulation for inhalation, which can be a solution, comprises from about 25 mg/ml to about 35 mg/ml of the antibody.

In one embodiment, the formulation with high anti IL-6R antibody concentration includes arginine and/or methionine as a stabilizers or excipient in the formulation.

In one embodiment, the arginine used in the present invention is selected from the group consisting of arginine per se, derivatives of arginine, and salts thereof. In one embodiment, the formulation includes L-arginine or a salt thereof. In one embodiment, the methionine used in the present invention is selected from the group consisting of methionine per se, derivatives of methionine, and salts thereof. In one embodiment, the formulation includes L-methionine or a salt thereof. In one embodiment, the antibody-containing liquid formulation according to the present invention contains arginine and does not contain methionine and the concentration of arginine ranges from about 25 mM to about 1500 mM. In one embodiment, the antibody-containing liquid formulation according to the present invention contains arginine and does not contain methionine and the concentration of arginine ranges from about 90 mM to about 1100 mM. In one embodiment, the antibody-containing liquid formulation according to the present invention contains arginine and does not contain methionine and the concentration of arginine ranges from about 150 mM to about 750 mM. In one embodiment, the antibody-containing liquid formulation according to the present invention contains arginine and methionine and the total concentration of arginine and methionine ranges from about 40 to about 1450 mM. In one embodiment, the antibody-containing liquid formulation according to the present invention contains arginine and methionine and the arginine concentration ranges from about 40 mM to about 1000 mM and the methionine concentration ranges from about 10 mM to about 200 mM. In one embodiment, the antibody-containing liquid formulation according to the present invention contains arginine and methionine and the arginine concentration ranges from about 50 mM to about 750 mM and the methionine concentration ranges from about 10 mM to about 100 mM. In one embodiment, the antibody-containing liquid formulation according to the present invention contains arginine and methionine and the arginine concentration ranges from about 100 mM to about 350 mM and the methionine concentration ranges from about 10 mM to about 50 mM.

In one embodiment, the antibody, for example, at the concentrations described or exemplified herein, is formulated with a buffered aqueous carrier. In one embodiment, the carrier comprises sterile water. In one embodiment, the buffered antibody formulation is in liquid form. In one embodiment, the liquid form is suitable for administration by soft mist inhalation or nebulization. The amount of water in the buffered formulation can vary in accordance with the desired volume to be administered. The buffer solution is prepared using a buffering agent which is a substance for maintaining a pH of the solution. In one embodiment, a high concentration antibody-containing liquid formulation according to the present invention has a pH ranging from about 5 to about 7. In one embodiment, a high concentration antibody-containing liquid formulation according to the present invention has a pH ranging from about 5.5 to about 6.5. In one embodiment, a high concentration antibody-containing liquid formulation according to the present invention has a pH of about 6. A suitable buffering agent is one which can adjust the pH in this range and which is pharmaceutically acceptable. Such buffering agents are known to those skilled in the art, and include, but are not limited to, inorganic salts, such as phosphoric acid salts (sodium or potassium) and sodium hydrogen carbonate; organic acid salts such as citric acid salts (sodium or potassium), sodium acetate and sodium succinate; and acids, such as phosphoric acid, carbonic acid, citric acid, succinic acid, malic acid, and gluconic acid. Tris buffers, Good's buffers, such as IVIES, MOPS and HEPES, histidine (e.g., histidine hydrochloric acid salt), and glycine can also be used. In one embodiment, the buffer is selected from the group consisting of a histidine buffer and a glycine buffer. In one embodiment, the buffer is a histidine buffer. In one embodiment, the concentration of the buffer ranges from about 1 mM to about 500 mM. In one embodiment, the concentration of the buffer ranges from about 5 mM to about 100 mM. In one embodiment, the concentration of the buffer ranges from about 10 mM to about 20 mM. In one embodiment, the buffer is a histidine buffer in a concentration ranging from about 5 mM to about 25 mM. In one embodiment, the buffer is a histidine buffer in a concentration ranging from about 10 mM to about 20 mM.

In one embodiment, the formulation according to the present invention further comprises a surfactant. Suitable surfactant include, but are not limited to, nonionic surfactants, for example, sorbitan fatty acid esters such as sorbitan monocaprylate, sorbitan monolaurate, and sorbitan monopalmitate; glycerin fatty acid esters such as glycerol monocaprylate, glycerol monomyristate and glycerol monostearate; polyglycerol fatty acid esters such as decaglyceryl monostearate, decaglyceryl distearate and decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate and polyoxyethylene sorbitan tristearate; polyoxyethylene sorbitol fatty acid esters such as polyoxyethylene sorbitol tetrastearate and polyoxyethylene sorbitol tetraoleate; polyoxyethylene glycerin fatty acid esters, such as polyoxyethylene glyceryl monostearate; polyethylene glycol fatty acid esters, such as polyethylene glycol distearate; polyoxyethylenealkyl ethers, such as polyoxyethylene lauryl ether, polyoxyethylene polyoxypropylene alkyl ethers, such as polyoxyethylene polyoxypropylene glycol ether, polyoxyethylene polyoxypropylene propyl ether and polyoxyethylene polyoxypropylene cetyl ether, polyoxyethylene alkyl phenyl ethers, such as polyoxyethylene nonylphenyl ether; polyoxyethylene hardened castor oils such as polyoxyethylene castor oil and polyoxyethylene hardened castor oil (polyoxyethylene hydrogenated castor oil); polyoxyethylene bees wax derivatives such as polyoxyethylene sorbitol bees wax; polyoxyethylenelanolin derivatives, such as polyoxyethylenelanolin; surfactants having an HLB of 6 to 18 such as polyoxyethylene fatty acid amides, for example, polyoxyethylene octadecanamide; anionic surfactants, for example, alkyl sulfate salts having a C=O or C=S alkyl group, such as sodium cetyl sulfate, sodium laurylsulfate and sodium oleyl sulfate: polyoxyethylenealkyl ether sulfate salts in which the average number of moles of the added ethylene oxide units is 2 to 4 and the number of carbon atoms of the alkyl group is 10 to 18, such as polyoxyethylenes; sodium lauryl sulfate; alkyl sulfosuccinate salts having a C=S alkyl group, such as sodium lauryl sulfosuccinate; natural surfactants such as lecithin and glycerophospholipids; sphingophospholipids such as sphingomyelin; and sucrose esters of fatty acids. These surfactants can be added to the formulation of the present invention individually, or two or more of these surfactants can be added in combination.

In one embodiment, the surfactant is selected from the group consisting of polyoxyethylene sorbitan fatty acid esters, polyoxyethylene polyoxypropylene alkyl ethers, and mixtures thereof. In one embodiment, the surfactant is selected from the group consisting of polysorbates 20, 21, 40, 60, 65, 80, 81, 85, and mixtures thereof. In one embodiment, the surfactant is a Pluronic type surfactant. In one embodiment, the surfactant is selected from the group consisting of polysorbate 20, polysorbate 80, Pluronic F-68 (Poloxamer 188), and mixtures thereof. In one embodiment, the amount of the surfactant(s) ranges from about 0.0001% to about 10% (w/v). In one embodiment, the amount of the surfactant(s) ranges from about 0.001% to about 5% (w/v). In one embodiment, the amount of the surfactant(s) ranges from about 0.005% to about 3% (w/v).

In one embodiment, the formulation includes a phosphate buffer comprising from about 5 mM to about 50 mM of sodium dihydrogen phosphate dehydrate. In one embodiment, the formulation includes a phosphate buffer comprising from about 5 mM to about 20 mM of sodium dihydrogen phosphate dehydrate. In one embodiment, the formulation includes a phosphate buffer comprising from about 10 mM to about 30 mM of sodium dihydrogen phosphate dehydrate. In one embodiment, the formulation includes a phosphate buffer comprising from about 25 mM to about 50 mM of sodium dihydrogen phosphate dehydrate. In one embodiment, the formulation includes a phosphate buffer comprising about 12.5 mM of sodium dihydrogen phosphate dehydrate.

In one embodiment, the formulation includes a phosphate buffer comprising from about 5 mM to about 50 mM of disodium phosphate dodecahydrate. In one embodiment, the formulation includes a phosphate buffer comprising from about 5 mM to about 10 mM of disodium phosphate dodecahydrate. In one embodiment, the formulation includes a phosphate buffer comprising from about 10 mM to about 30 mM of disodium phosphate dodecahydrate. In one embodiment, the formulation includes a phosphate buffer comprising from about 25 mM to about 50 mM of disodium phosphate dodecahydrate. In one embodiment, the formulation includes a phosphate buffer comprising about 12.5 mM of disodium phosphate dodecahydrate.

The pharmaceutical formulations disclosed herein are especially suitable for soft mist inhalation or nebulization, which provide good lung deposition, typically up to 55-60%, and provide better drug bioavailability at the site of action compared to administration by intravenous infusion, and are particularly advantageous for treating COVID-19 infections. Administration of a therapeutic monoclonal antibody by liquid inhalation is to treat a respiratory viral infection, particularly a COVID-19 infection, is superior compared to intravenous administration.

Soft mist inhalers that nebulize a small amount of a liquid formulation containing the required dosage of therapeutic monoclonal antibody into an aerosol within a few seconds are suitable for administering the formulations of the invention by inhalation. These soft mist inhaler is particularly suitable to the liquid formulation disclosed in the current invention.

In one embodiment, the soft mist inhalation device used to administer the aqueous biopharmaceutical formulation of the present invention nebulizes less than 30 microliters of the biopharmaceutical formulation to provide an aerosol that contains a therapeutically effective quantity of the drug. In one embodiment, the average particle size of the aerosol formed from one puff is less than about 10 micrometers. In one embodiment, the average particle size of the aerosol formed from one puff is less than about 5 micrometers. The biopharmaceutical formulation in the soft mist inhaler is converted by the inhaler into an aerosol destined for deposition in the lungs. The formulation, which can be a solution, is stored in a reservoir in the soft mist inhaler. The formulation does not contain any ingredients which might interact with the inhaler to affect the quality of the solution or of the aerosol produced. In addition, active substances in biopharmaceutical formulations are very stable when stored at 2° C. to 8° C. and can be administered directly.

In one embodiment, the inhalation device is a soft mist inhaler. In one embodiment, the formulations containing the therapeutic monoclonal antibody tocilizumab are administered using an inhaler of the kind described herein. Here we should once again briefly mention the patent documents described hereinbefore, to which reference is hereby made.

A soft mist inhaler device of this kind for the propellant-free administration of a metered amount of a liquid biopharmaceutical composition for soft mist inhalation is described in detail in, for example, US20190030268, entitled "inhalation atomizer comprising a blocking function and a counter".

The biopharmaceutical formulation in the nebulizer is converted into aerosol destined for the lungs. The nebulizer uses high pressure to spray the biopharmaceutical formulation, which can be a solution.

The soft mist inhalable device can be carried anywhere by the patient, since it has a cylindrical shape and handy size of about 8 cm to 18 cm long, and about 2.5 cm to 5 cm wide. The nebulizer sprays a defined volume of the pharmaceutical formulation through small nozzles at high pressures, so as to produce inhalable aerosols.

Figure 1:
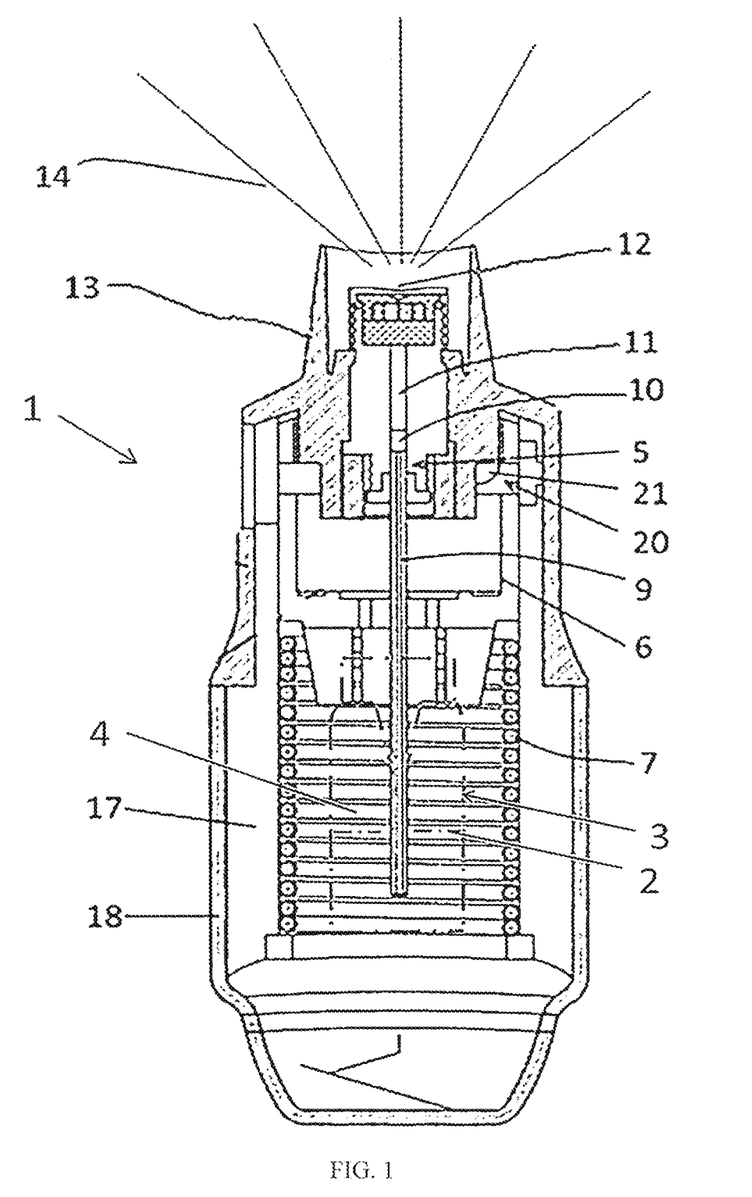
FIG. 1 shows a longitudinal section through an atomizer in the stressed state.

In one embodiment, the delivery device comprises an atomizer 1, a fluid 2, a vessel 3, a fluid compartment 4, a pressure generator 5, a holder 6, a drive spring 7, a delivering tube 9, a non-return valve 10, pressure room 11, a nozzle 12, a mouthpiece 13, an aerosol 14, an air inlet 15, an upper shell 16, and an inside part 17.

The inhalation atomizer 1 comprising the block function and the counter described above for spraying a medicament fluid 2 is depicted in the FIG. 1 in a stressed state. The atomizer 1 comprising the block function and the counter described above is preferably a portable inhaler and propellant-free.

FIG. 1 shows a longitudinal section through the atomizer in a stressed state.

For the typical atomizer 1 comprising the block function and the counter described above, an aerosol 14 that can be inhaled by a patient is generated through the atomization of the fluid 2, which is preferably formulated as a medicament liquid. The medicament is typically administered at least once a day, more specifically multiple times a day, preferably at predestined time gaps, according to how serious the illness affects the patient.

In an embodiment, the atomizer 1 described above has substitutable and insertable vessel 3, which contains the medicament fluid 2. Therefore, a reservoir for holding the fluid 2 is formed in the vessel 3. Specifically, the medicament fluid 2 is located in the fluid compartment 4 formed by a collapsible bag in the vessel 3.

In an embodiment, the amount of fluid 2 for the inhalation atomizer 1 comprising the block function and the counter described above is in the vessel 3 to provide, e.g., up to 200 doses. A classical vessel 3 has a volume of 2 to 10 ml. A pressure generator 5 in the atomizer 1 is used to deliver and atomize the fluid 2 in a predetermined dosage amount. Therefore, the fluid 2 can be released and sprayed in individual doses, specifically from 5 to 30 microliter.

In an embodiment, the atomizer 1 described above may have a pressure generator 5 and a holder 6, a drive spring 7, a delivering tube 9, a non-return valve 10, a pressure room 11, and a nozzle 12 in the area of a mouthpiece 13. The vessel 3 is latched by the holder 6 in the atomizer 1 so that the delivering tube 9 is plunged into the vessel 3. The vessel 3 could be separated from the atomizer 1 for substitution.

In an embodiment, when drive spring 7 is stressed in an axial direction, the delivering tube 9, the vessel 3 along with the holder 6 will be shifted downwards. Then the fluid 2 will be sucked into the pressure room 11 through delivering tube 9 and the non-return valve 10.

In one embodiment, after releasing the holder 6, the stress is eased. During this process, the delivering tube 9 and closed non-return valve 10 are shifted back upward by releasing the drive spring 7. Consequently, the fluid 2 is under pressure in the pressure room 11. Then the fluid 2 is pushed through the nozzle 12 and atomized into an aerosol 14 by the pressure. A patient could inhale the aerosol 14 through the mouthpiece 13, while the air is sucked into the mouthpiece 13 through air inlets 15.

The inhalation atomizer 1 described above has an upper shell 16 and an inside part 17, which can be rotated relative to the upper shell 16. A lower shell 18 is manually operable to attach onto the inside part 17. The lower shell 18 can be separated from the atomizer 1 so that the vessel 3 can be substituted and inserted.

In one embodiment, the inhalation atomizer 1 described above has the lower shell 18, which carries the inside part 17, being rotatable relative to the upper shell 16. As a result of rotation and engagement between the upper unit 17 and the holder 6, through a gear 20, the holder 6 is axially moved counter to the force of the drive spring 7 and the drive spring 7 is stressed.

In an embodiment, in the stressed state, the vessel 3 is shifted downwards and reaches to a final position, which is demonstrated in the FIG. 1. The drive spring 7 is stressed under this final position. Then the holder 6 is clasped. Therefore, the vessel 3 and the delivering tube 9 are prevented from moving upwards so that the drive spring 7 is stopped from easing.

In an embodiment, the atomizing process occurs after releasing the holder 6. The vessel 3, the delivering tube 9 and the holder 6 are shifted back by the drive spring 7 to the beginning position. This is referred to herein as major shifting in here. While the major shifting occurs, the non-return valve 10 is closed and the fluid 2 is under pressure in the pressure room 11 by the delivering tube 9, and fluid 2 is pushed out and atomized by the pressure.

In an embodiment, the inhalation atomizer 1 described above may have a clamping function. During clamping, the vessel 3 preferably performs a lifting shift for withdrawal of fluid 2 during the atomizing process. The gear 20 has sliding surfaces 21 on the upper shell 16 and/or on the holder 6, which makes holder 6 move axially when the holder 6 is rotated relative to the upper shell 16.

In an embodiment, the holder 6 is not blocked for too long and can perform the major shifting. Therefore, the fluid 2 is pushed out and atomized.

In an embodiment, when the holder 6 is in the clamping position, the sliding surfaces 21 move out of engagement. Then the gear 20 releases the holder 6 for the opposite shift axially.

Figure 2:
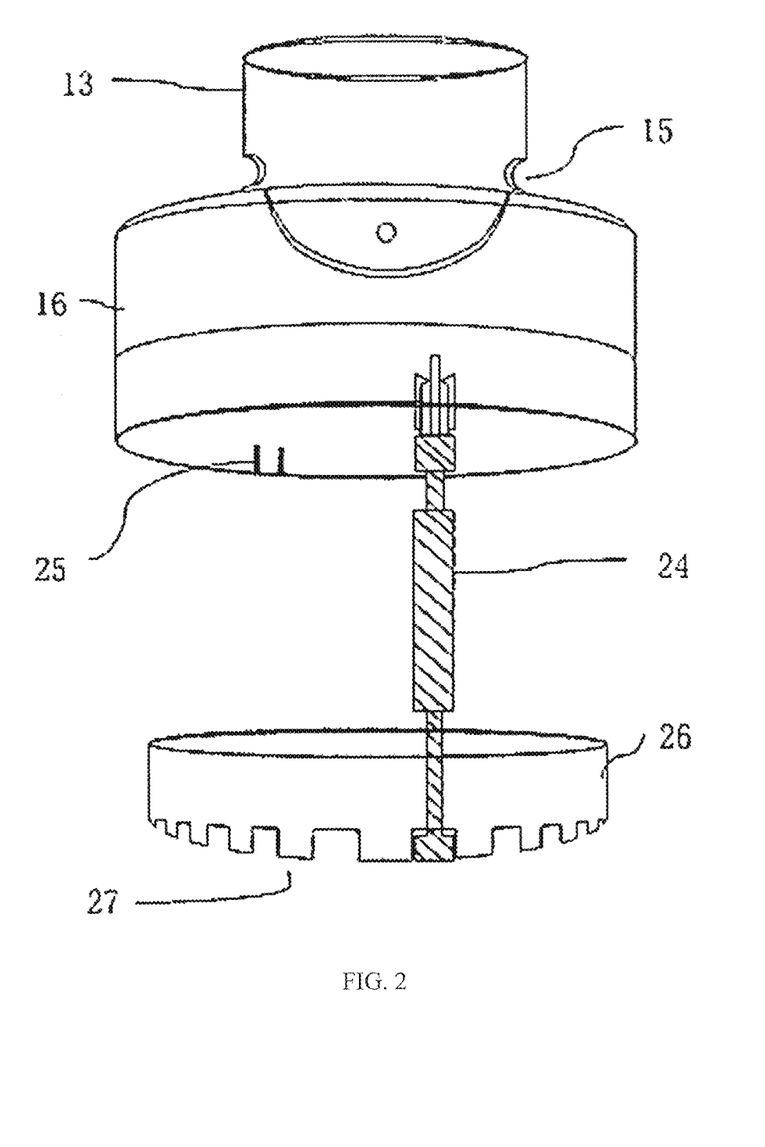
FIG. 2 shows a counter element of the atomizer.

In an embodiment, the atomizer 1 preferably includes a counter element shown in FIG. 2. The counter element has a worm 24 and a counter ring 26. Preferably, the counter ring 26 is circular and has dentate part at the bottom. The worm 24 has upper and lower end gears. The upper end gear contacts with the upper shell 16. The upper shell 16 has inside bulge 25. When the atomizer 1 is employed, the upper shell 16 rotates; and when the bulge 25 passes through the upper end gear of the worm 24, the worm 24 is driven to rotate. The rotation of the worm 24 drives the rotation of the counter ring 26 through the lower end gear so as to result in a counting effect.

In an embodiment, the locking mechanism is realized mainly by two protrusions. Protrusion A is located on the outer wall of the lower unit of the inside part. Protrusion B is located on the inner wall of counter. The lower unit of the inside part is nested in the counter. The counter can rotate relative to the lower unit of the inside part. Because of the rotation of the counter, the number displayed on the counter can change as the actuation number increases, and can be observed by the patient. After each actuation, the number displayed on the counter changes. Once a predetermined number of actuations is achieved, Protrusion A and Protrusion B will encounter with each other and hence the counter will be prevented from further rotation. Therefore, the atomizer is blocked and stopped from further use. The number of actuations of the device can be counted by the counter.

Atomization devices include, but are not limited to, soft mist inhalers, ultrasonic atomizers, air compression atomizers, and mesh-based atomizers.

The nebulizer described above is suitable for nebulizing the formulations according to the invention to form an aerosol suitable for inhalation. Nevertheless, the formulation according to the invention can also be nebulized using other inhalers apart from those described above, including, but not limited to, an ultrasonic nebulizer, a jet nebulizer, or a mesh nebulizer.

The effectiveness of a soft mist inhaler can be tested using an in vitro system in which a therapeutic monoclonal antibody formulation, which can be a solution, is aerosolized and the soft mist is caught in a so-called "trap." The activity of the therapeutic antibody in the aerosol reservoir (a) can be compared with its activity in the trapped liquid (b), e.g. by means of an immunoassay or an assay for the biological effectiveness of the antibody. Such an experiment makes it possible to evaluate the degree of destruction of the functional antibody drug by the nebulizing process. A second parameter used to characterize the aerosol is the so-called inhalable proportion, which is defined herein as the proportion of the mist droplets with a measured mass median aero-dynamic diameter (MMAD) of less than about 10 micrometer. The inhalable proportion can be measured using an "Andersen Impactor." For good protein inhalation and absorption it is important to not only to achieve aerosolization without any substantial loss of activity but to also generate an aerosol with a good inhalable proportion. Aerosols with an MMAD of less than about 5 micrometer are significantly better at reaching the alveoli where their chances of being absorbed are significantly greater. The effectiveness of a soft mist inhalation device can also be tested in an in vivo system; in this type of test factors such as susceptibility to lung proteases come into play. As an example of an in vivo test system, a protein containing mist is administered to a dog through a tracheal tube. Blood samples are then taken at suitable time intervals and the protein level in the plasma is then measured by an immunological or biological method.

An advantage of the claimed invention is its surprising ability to nebulize concentrated solutions of biologically active macromolecules without any substantial loss of biological activity.

EXAMPLES

Formulation Ingredients:
Anti-IL-6 receptor antibody, tocilizumab.
Polysorbate 80.
L-Arginine hydrochloride.
L-Methionine.
L-Histidine.
Sucrose.
Sodium dihydrogen phosphate dehydrate.
Disodium phosphate dodecahydrate.

Example 1

A formulation of an aqueous solution containing the anti-IL-6 receptor antibody tocilizumab as an active ingredient in combination with excipients for administration using a soft mist inhaler and/or nebulizer is prepared containing the components provided in Table 1. A stock solution containing the excipients is prepared at a 10-50 times higher concentration than in the formulation containing the therapeutic monoclonal antibody. The stock solution is then diluted to bring it to desired concentration.

TABLE 1

Components of Sample 1

| Ingredients | Sample 1 |
| --- | --- |
| Anti-IL-6 receptor antibody (Tocilizumab) | 150 mg |
| Polysorbate 80 | 2.5 mg |
| L-Arginine hydrochloride | 35.5 mg |
| L-Methionine | 5.5 mg |
| L-Histidine | 10.5 mg |
| pH | 6 |
| Water for injection | 5 ml |

Example 2

A formulation of an aqueous solution containing the anti-IL-6 receptor antibody tocilizumab as an active ingredient in combination with excipients for administration using a soft mist inhaler and/or nebulizer is prepared containing the components provided in Table 2. A stock solution containing the excipients is prepared at a 10-50 times higher concentration than in the formulation containing the therapeutic monoclonal antibody. The stock solution is then diluted to bring it to desired concentration.

TABLE 2

Components of Sample 2 and Sample 3

| Ingredients | Sample 2 | Sample 3 |
| --- | --- | --- |
| anti-IL-6 receptor antibody (Tocilizumab) | 50 mg | 100 mg |
| Polysorbate 80 | 0.5 mg | 1 mg |
| L-Arginine hydrochloride | 11.83 mg | 23.66 mg |
| L-Methionine | 1.8 mg | 3.6 mg |
| L-Histidine | 3.5 mg | 7 mg |
| pH | 6 | 6 |
| Water for injection | 5 ml | 5 ml |

Example 3

A formulation of an aqueous solution containing the anti-IL-6 receptor antibody tocilizumab as an active ingredient in combination with excipients for administration using a soft mist inhaler and/or nebulizer is prepared containing the components provided in Table 3. A stock solution containing the excipients is prepared at a 10-50 times higher concentration than in the formulation containing the therapeutic monoclonal antibody. The stock solution is then diluted to bring it to desired concentration.

TABLE 3

Components of Sample 4 and Sample 5

| Ingredients | Sample 4 | Sample 5 |
|---|---|---|
| anti-IL-6 receptor antibody (Tocilizumab) | 50 mg | 100 mg |
| Polysorbate 80 | 1.0 mg | 2.0 mg |
| Disodium phosphate dodecahydrate | 30 mg | 30 mg |
| Sodium dihydrogen phosphate dehydrate | 10 mg | 10 mg |
| Sucrose | 125 mg | 250 mg |
| pH | 6 | 6 |
| Water for injection | 5 ml | 5 ml |

Example 4

Aerodynamic Particle Size Distribution:

The aerodynamic particle size distribution was determined using a Next Generation Pharmaceutical Impactor (NGI). The sample tested is Sample 5 in Example 3.

The device is soft mist inhaler, which is disclosed in US20190030268, "inhalation atomizer comprising a blocking function and a counter".

The device was held close to the NGI inlet until no aerosol was visible. The flow rate of the NGI was set to 30 L/minute and was operated under ambient temperature and a relative humidity (RH) of 90%.

The solution of Sample 5 in Example 3 was discharged into the NGI. Fractions of the dose were deposited at different stages of the NGI, in accordance with the particle size of the fraction. Each fraction was washed from the stage and analyzed using HPLC.

The result is shown in Table 4.

TABLE 4

Aerodynamic particle size distribution of Sample 5 in Example 3

| Deposited | Tocilizumab Dosage (μg) | Tocilizumab Percentage content at all levels % | Cut-off diameters at 30 L/min (μm) |
|---|---|---|---|
| Throat | 76.50 | 18.12 | |
| Stage 1 | 19.03 | 4.51 | 11.72 |
| Stage 2 | 63.74 | 15.10 | 6.4 |
| Stage 3 | 106.30 | 25.18 | 3.99 |
| Stage 4 | 97.46 | 23.09 | 2.30 |
| Stage 5 | 42.31 | 10.02 | 1.36 |
| Stage 6 | 10.53 | 2.49 | 0.83 |
| Stage 7 | 2.02 | 0.48 | 0.54 |
| MOC | 4.29 | 1.02 | |
| Theoretical dose (μg) | | 442 | |
| Actual test dose (μg) | | 422.18 | |
| Recovery rate (%) | | 95.52 | |
| ISM(μg) | | 326.65 | |
| FPD(μg) | | 262.91 | |
| FPF(%) | | 62.28 | |

MOC is Micro-Orifice Collector.
ISM is Impactor Size Mass.
FPF is Fine Particle Fraction.
FPD is fine particle dose.

Example 5

Stability Studies:
The sample being tested is Sample 5 of Example 3.

TABLE 5

Accelerated and Long Term Stability of Sample 5 (conditions: 25° C. ± 2° C./60% RH ± 5% RH)

| | Accelerated Storage Condition (25° C. ± 2° C./60% RH ± 5% RH) | | | | |
|---|---|---|---|---|---|
| | Initial | 1 month | 2 months | 3 months | 6 months |
| Content Description | Clear to opalescent, colorless to pale yellow | Clear to opalescent, colorless to pale yellow | Clear to opalescent, colorless to pale yellow | Clear to opalescent, colorless to pale yellow | Clear to opalescent, colorless to pale yellow |
| Tocilizumab Content (% w/w) | 99.8 | 99.6 | 99.1 | 98.7 | 97.4 |
| pH | 6.12 | 6.2 | 6.15 | 6.18 | 6.21 |
| Molecular weight | Complies | Complies | Complies | Complies | Complies |
| Free thiols | Complies | Complies | Complies | Complies | Complies |
| High molecular weight impurities | Complies | Complies | Complies | Complies | Complies |
| Low molecular weight impurities | Complies | Complies | Complies | Complies | Complies |

TABLE 6

Accelerated and Long Term Stability of Sample 5 (conditions: 2-8° C./25% RH ± 5% RH)

| | Long Term Storage Condition (2-8° C./25% RH ± 5% RH) | | |
|---|---|---|---|
| | Initial | 3 months | 6 months |
| Content Description | Clear to opalescent, colorless to pale yellow | Clear to opalescent, colorless to pale yellow | Clear to opalescent, colorless to pale yellow |
| Tocilizumab Content (% w/w) | 99.8 | 99.8 | 99.1 |
| pH | 6.12 | 6.11 | 6.17 |
| Molecular weight | Complies | Complies | Complies |
| Free thiols | Complies | Complies | Complies |
| High molecular weight impurities | Complies | Complies | Complies |
| Low molecular weight impurities | Complies | Complies | Complies |

As shown in Tables 5 and 6, at pH 6.12 the Tocilizumab solutions showed good stability. Tocilizumab solutions were stable for about 6 months at 2-8° C./25% RH±5% RH.

What is claimed is:
1. A pharmaceutical formulation comprising an aqueous solution comprising:
    tocilizumab in an amount ranging from about 5 mg/mL to about 30 mg/mL,
    histidine in a concentration ranging from about 5 mM to about 25 mM,
    arginine in an amount ranging from about 100 mM to about 350 mM,
    methionine in an amount ranging from about 10 mM to about 50 mM, and polysorbate 80 in an amount ranging from about 0.005% to about 3% (w/v), wherein the pH of the pharmaceutical formulation ranges from about 5 to about 7, and wherein the formulation is contained within a device for administration by nebulization.

2. A method for administering the pharmaceutical formulation of claim 1 comprising nebulizing a defined amount of the pharmaceutical formulation with an inhaler by using pressure to force the pharmaceutical formulation through a nozzle to form an inhalable aerosol.

3. The method of claim 2, wherein the defined amount of the pharmaceutical formulation is less than about 70 microliters.

4. The method of claim 3, wherein the average particle size of the aerosol is less than about 15 microns.

5. A method of treating COVID-19 in a patient comprising administering the pharmaceutical formulation of claim 1 to the patient by inhalation.

* * * * *